(12) United States Patent
Baumann et al.

(10) Patent No.: US 7,639,786 B2
(45) Date of Patent: Dec. 29, 2009

(54) X-RAY OPTICAL TRANSMISSION GRATING OF A FOCUS-DETECTOR ARRANGEMENT OF AN X-RAY APPARATUS FOR GENERATING PROJECTIVE OR TOMOGRAPHIC PHASE CONTRAST RECORDINGS OF A SUBJECT

(75) Inventors: Joachim Baumann, München (DE); Christian David, Lauchringen (DE); Martin Engelhardt, München (DE); Jörg Freudenberger, Eckental (DE); Eckhard Hempel, Fürth (DE); Martin Hoheisel, Erlangen (DE); Thomas Mertelmeier, Erlangen (DE); Franz Pfeiffer, Brugg (CH); Stefan Popescu, Erlangen (DE); Manfred Schuster, München (DE)

(73) Assignee: Siemens Aktiengesellschaft, Munich (DE)

( * ) Notice: Subject to any disclaimer, the term of this patent is extended or adjusted under 35 U.S.C. 154(b) by 180 days.

(21) Appl. No.: 11/700,139

(22) Filed: Jan. 31, 2007

(65) Prior Publication Data

US 2007/0183579 A1    Aug. 9, 2007

(30) Foreign Application Priority Data

Feb. 1, 2006  (DE)  .................. 10 2006 004 604
Feb. 1, 2006  (DE)  .................. 10 2006 004 976
Aug. 9, 2006  (DE)  .................. 10 2006 037 281

(51) Int. Cl.
*G21K 1/00* (2006.01)
*G21K 1/10* (2006.01)

(52) U.S. Cl. ........................... 378/145; 378/5

(58) Field of Classification Search .................. 378/4, 378/5, 9, 15, 16, 19, 82, 85; 356/305, 328, 356/517, 518, 521; 250/201.9, 550, 234–236, 250/237 R, 237 G
See application file for complete search history.

(56) References Cited

U.S. PATENT DOCUMENTS 5,812,629 A * 9/1998 Clauser ...................... 378/62
2003/0081316 A1 5/2003 Goldberg et al.

(Continued)

FOREIGN PATENT DOCUMENTS

DE   10 2006 015 355.3   8/2007

(Continued)

OTHER PUBLICATIONS

Weitkamp et at., "X-ray phase imaging with a grating interferometer", Optics Express 2005, vol. 12, No. 16, pp. 6296-6304.

(Continued)

*Primary Examiner*—Edward J Glick
*Assistant Examiner*—Anastasia Midkiff
(74) *Attorney, Agent, or Firm*—Harness, Dickey & Pierce, P.L.C.

(57) ABSTRACT

An X-ray optical transmission grating of a focus-detector arrangement of an X-ray apparatus is disclosed, for generating projective or tomographic phase contrast recordings of a subject. In at least one embodiment, the grating includes a multiplicity of grating bars and grating gaps arranged periodically on at least one surface of at least one wafer, wherein the X-ray optical transmission grating includes at least two sub-gratings arranged in direct succession in the beam direction.

18 Claims, 5 Drawing Sheets

U.S. PATENT DOCUMENTS

2005/0207012 A1     9/2005     Arnold et al.

FOREIGN PATENT DOCUMENTS

| DE | 10 2006 015 356.1 | 8/2007 |
| --- | --- | --- |
| DE | 10 2006 015 358.8 | 8/2007 |
| DE | 10 2006 017 290.6 | 8/2007 |
| DE | 10 2006 017 291.4 | 8/2007 |
| EP | 1 260 869 A1 | 11/2002 |
| EP | 1 447 046 A1 | 8/2004 |

OTHER PUBLICATIONS

D. Vaughan (ed.), "X-Ray Data Booklet", Lawrence Berkeley Laboratory, Berkley, 1986, pp. 2-28, 2-29.
U. Bonse and M. Hart, "An X-ray Interferometer", Appl. Phys. Lett., 1965, vol. 6, No. 8, pp. 155-156.
Ingal and Beliaevskaya, "X-ray plane-wave topography observation of the phase contrast from a non-crystalline object", J. Phys. D: Appl. Phys. 28, 1995, pp. 2314-2317.
R. Fitzgerald, "Phase-Sensitive X-Ray Interferometer", Physics Today, 53, 2000, pp. 23-26.
Chapman et al., "Diffraction enhanced x-ray imaging", Phys. Med. Biol. 42, 1997, pp. 2015-2025.
Wilkins eta., "Phase-contrast imaging using polychromatic hard X-rays", Nature 384, 1996, pp. 335-338.
V. Lehmann, The Physics of Macropore Formation in low Doped n-Type Silicon, J. Electrochemical Soc. 140 (10), 1993, pp. 2836-2843.
Bergmann, Schäfer, "Lehrbuch der Experimentalphysik", vol. 1, Mechanik, Akustik, Wärme, De Gruyter, Berlin, 1970, pp. 542-554.
Shack et al., J. Opt. Soc. Am. 61, 1971, p. 656.
Platt et al., "History and Principles of Shack-Hartmann Wavefront Sensing", Journal of Refractive Surgery, vol. 17, 2001, pp. 573-577.
F. Roddier, "Variations on a Hartmann theme", Opt. Eng. 29, 1990, pp. 1239-1242.
Primot et al., "Deconvolution from wave-front sensing: a new technique for compensating turbulence-degraded images", J. Opt. Soc. Am. 7(9), 1990, pp. 1598-1608.
J. C. Wyant, "White Light Extended Source Shearing Interferometer", Appl. Opt. 13, 1974, pp. 200-202.
C. L. Koliopoulos, "Radial grating lateral shear heterodyne interferometer", Appl. Opt. 19, 1980, pp. 1523-1528.
J. Primot, L. Songo, "Achromatic three-wave (or more) lateral shearing interferometer", J. Opt. Soc. Am. A, 12(12), 1995, pp. 2679-2685.
J. Primot, "Theoretical description of Shack-Hartmann wave-front sensor". Optics Communications, 222, 2003, pp. 81-92.
V. Ronchi, "Forty Years of History of a Grating Interferometer", Appl. Opt., 3(4), 1964, pp. 437-451.
Schroer et al., "Hard x-ray nanoprobe based on refractive x-ray lenses", Appl. Phys. Lett. 87, 124103, 2005.
M. Bavdaz, N. Gurker, "Coded Imaging X-ray Microprobe", X-Ray Spectrometry, 22, 1993, pp. 65-70.
Momose et al. "Tomographic image reconstruction using X-ray phase information", SPIE, vol. 2708, pp. 674-684.
Barty et al., "Time-gated medical imaging with ultrafast laser plasma x-rays", SPIE, vol. 2523, pp. 286-298.
C. J. Kotre, I. P. Birch, "Phase contrast enhancement of x-ray mammography: a design study", Phys. Med. Biol., 44, 1999, pp. 2853-2866.
Arfelli et al, "Low-dose phase contrast x-ray medical imaging", Phys. Med. Biol. 43. 1998, pp. 2845-2852.
Herrlin et al., "Contrast-Enhanced Radiography by Differential Absorption Using a Laser-Produced X-Ray Source", Investigative Radiology 32, 1997, pp. 306-310.
Grätz et al., "Time-Gated Imaging in Radiology: Theoretical and Experimental Studies", IEEE J. of selected Topics in Quantum Electronics, 2(4), 1996, pp. 1041-1048.
Murnane et al., "Ultrafast X-ray Pulses from Laser-Produced Plasmas", Science, vol. 251, 1991, pp. 531-536.
Krol et al., "Laser-based microfocused x-ray source for mammography: Feasibiliy study", Med. Phys. 24(5), 1997, pp. 725-732.
Piestrup et al., "A design of mammography units using a quasiminichromatic x-ray source", Review of Scientific Instruments, 72(4), 2001, pp. 2159-2170.
C. G. Schroer, B. Lengler, "Focusing Hard X Rays to Nanometer Dimensions by Adiabatically Focusing Lenses", Phys. Rev. Lett. 94, 054802, 2005.
Weitkamp, Timm; Diaz, Ana; David, Christian. X-ray phase imaging with a grating interferometer. Optics Express. Aug. 08, 2005, vol. 13, No. 16, p. 6296-6304.
D. Vaughan. X-Ray Data Booklet. Lawrence Berkeley Laboratory, Berkeley, 1986. p. 2-28.
R. Fitzgerald. Phase-Sensitive X-Ray Imaging. Physics Today, 53 (2000), p. 23-26.
U. Bonse; M. Hart. An X-ray Interferometer. Appl. Phys. Lett. 6 (1965), p. 155-156.
D. Chapman; W. Thomlinson; R.E. Johnston; D. Washburn; E. Pisano; N. Gmür: Z. Zhong; R. Menk; F. Arfelli; D. Sayers. Diffraction enhanced x-ray imaging. Phys. Med. Biol. 42 (1997), p. 2015-2025.
V.N. Ingal; E.A. Beliaevskaya. X-ray plane-wave topography observation of the phase contrast from a non-crystalline object. J. Phys. D: Appl. Phys. 28 (1995), p. 2314-2317.
S.W. Wilkins; T.E. Gureyev; D. Gao; A. Pogany; A.W. Stevenson. Phase-contrast imaging using polychromatic hard X-rays. Nature 384 (1996), p. 335-338, German Office Action.

* cited by examiner

X-RAY OPTICAL TRANSMISSION GRATING OF A FOCUS-DETECTOR ARRANGEMENT OF AN X-RAY APPARATUS FOR GENERATING PROJECTIVE OR TOMOGRAPHIC PHASE CONTRAST RECORDINGS OF A SUBJECT

PRIORITY STATEMENT

The present application hereby claims priority under 35 U.S.C. §119 on German patent application numbers DE 10 2006 004 604.8 filed Feb. 1, 2006, DE 10 2006 004 976.4 filed Feb. 1, 2006, and DE 10 2006 037 281.6 filed Aug. 9, 2006, the entire contents of each of which is hereby incorporated herein by reference.

FIELD

Embodiments of the invention generally relate to an X-ray optical transmission grating of a focus-detector arrangement of an X-ray apparatus for generating projective or tomographic phase contrast recordings of a subject. For example, they may relate to one having a multiplicity of grating bars and grating gaps arranged periodically on at least one surface of at least one wafer.

BACKGROUND

Transmission gratings for generating projective or tomographic phase contrast recordings of a subject are widely known. By way of example, reference is made to the European patent application EP 1 447 046 A1 and the German patent applications (not yet published that the priority date of the present application) with the file references 10 2006 017 290.6, 10 2006 015 358.8, 10 2006 017 291.4, 10 2006 015 356.1 and 10 2006 015 355.3.

For imaging by ionizing rays, in particular X-rays, principally two effects can be observed which occur when the radiation passes through matter, namely the absorption and the phase shift of the radiation passing through a subject. It is known that in many cases, the phase shift when a ray passes through a subject depends much more strongly on small differences in the thickness and composition of the penetrated matter than the absorption effects do. Structures of a subject, it particular the soft structures of a patient, can thereby be recognized better.

For such phase contrast radiography or phase contrast tomography, the phase shift due to the object must be evaluated. Here, similarly as conventional absorption contrast X-radiography or absorption contrast X-ray tomography, both projective images of the phase shift can be compiled or even tomographic representations of the phase shift can be calculated from a multiplicity of projective images.

The phase of an X-ray wave cannot be determined directly, rather only by interference with a reference wave. The phase shifts relative to reference waves or neighboring rays can be measured by using interferometric gratings. In respect of interferometric measurement methods, reference is made to the documents cited above. In these methods, coherent X-radiation is passed through a subject, then delivered through a phase grating with a period adapted to the wavelengths of the radiation so as to create an interference pattern, which is phase shifted depends on the phase shift occurring in the object. This interference pattern is measured by a subsequent analysis-detector arrangement, so that the phase shift can be determined with position resolution.

The following should essentially be pointed out in this regard:

The emission of X-ray photons from laboratory X-ray sources as well as by conventional synchrotron radiation sources of the first to third generations is subject to stochastic processes. The emitted X-radiation therefore has no spatial coherence per se. In phase contrast radiography and tomography or any interference experiment, however, the radiation of X-ray sources behaves as coherent radiation when the observation angle at which the source appears to the observer or the object, the grating or the detector, is sufficiently small. The so-called spatial coherence length $L_c$ can be provided as a measure of the spatial or transverse coherence of an extended X-ray source $$L_c = \lambda \frac{a}{s}. \tag{1}$$

Here, $\lambda$ is the wavelength, s is the transverse source size and a is the source-observation point distance. Many authors also refer to half the above-defined value as the spatial coherence length. The exact value is incidental; what is important is that the coherence length $L_c$ is large compared to the (transverse) dimension of the spatial region from which rays are intended to interfere with one another.

In the context of the patent application, the term coherent radiation is intended to mean radiation which leads to the formation of an interference pattern under the given geometries and given distances of the X-ray optical gratings. It is self evident that the spatial coherence and therefore the spatial coherence length is always determined by the trio of quantities: wavelength, source size and observation distance. With a view to compact formulation, this fact has been abbreviated to terms such as "coherent X-radiation", "coherent X-radiation source" or "point source for generating coherent X-radiation". The basis for these abbreviations is that the wavelength or the energy E of the X-radiation in the applications discussed here is limited by the desired penetratability of the subject on the one hand and the spectrum available in laboratory X-ray sources on the other hand. The distance a between the source and the observation point is also subject to certain restrictions in laboratory equipment for nondestructive material testing or medical diagnosis. This usually leaves only the source size s as a single degree of freedom, even though the relationships between source size and tube power set narrow limits here.

The requirement for a small or point-like radiation source means that the available intensity is also relatively low. In order to increase the intensity, it has therefore also been proposed to use an X-ray source with a relatively large-area focus and to place an X-ray optical absorption grating, a so-called source grating, in the beam path between the focus and the subject. The large-area focus makes it possible to use larger and therefore more powerful X-ray sources. The narrow slits or gaps of the source grating ensure that all the rays, which have to emerge from the same slit, comply with the requisite spatial coherence. The slit width must satisfy the size requirement given by Equation (1) for the transverse source size s. Correct superposition, at least in terms of intensity, of the maxima and minima of the standing wave field is possible between the photons from slit to slit of the source grating with suitable tuning of the source grating period $g_0$ and the interference pattern period $g_2$ as well as the distance l between the source grating $G_0$ and the phase grating $G_1$ and the distance d between the phase grating $G_1$ and the interference pattern, according to:

$$g_0/g_2 = 1/d. \quad (2)$$

In the abbreviated formulation of the patent application, the term "quasi-coherent radiation" or "quasi-coherent radiation source" is used in this context.

The temporal or longitudinal coherence of the radiation is associated with the monochromaticity of the X-radiation or of the X-radiation source. The X-radiation of intense characteristic lines usually has a sufficient monochromaticity or temporal coherence length for the applications discussed here. Upstream monochromators or selection of the resonant energy via the bar height of the phase grating can also filter out a sufficiently narrow spectral range from a Bremsstrahlung spectrum or synchrotron spectrum, and thus satisfy the requirements for the temporal coherence length in the present arrangements.

A problem with these X-ray optical transmission gratings is that the production of such gratings, which require a large aspect ratio (=ratio of the bar height to width of the grating gap), is very elaborate. Furthermore, the precision of the production deteriorates significantly with an increasing aspect ratio.

SUMMARY

In at least one embodiment of the invention, an X-ray optical transmission grating is provided which allows simpler production.

The Inventors, in at least one embodiment, have discovered that without compromising the effect of an X-ray optical transmission grating, it is possible to form this grating from a multiplicity of sub-gratings. A particular X-ray optical grating with a particular function can thus be replaced by a plurality of sub-gratings arranged in direct succession, the sum of the sub-gratings fulfilling the function of the original one grating. In this way, it is possible to reduce the grating bar height according to the number of sub-gratings used, the width of the grating gaps remaining the same, so that the aspect ratio of bar height to width of the grating gaps is drastically reduced.

The inventors, in at least one embodiment, therefore propose that an X-ray optical transmission grating of a focus-detector arrangement of an X-ray apparatus for generating projective or tomographic phase contrast recordings of a subject, having a multiplicity of grating bars and grating gaps arranged periodically on at least one surface of at least one wafer, should be refined so that the X-ray optical transmission grating is composed of at least two sub-gratings arranged in direct succession in the beam direction.

Advantageously, for example, the transmission grating may be configured so that the grating bars and grating gaps of two sub-gratings are arranged on the two sides of one wafer. A wafer is thus used whose front and rear side is up both designed as gratings. At least with respect to these two sub-gratings, this also obviates the problem of aligning the grating bars and grating gaps during installation in the X-ray apparatus. They are already arranged correspondingly during the production process, and cannot become displaced relative to one another.

In order to align the gratings which are applied on the front and rear sides of a wafer, it is conceivable to employ the grating properties of the first grating when the structures for the second grating are being written by lithography. The gratings are partially transparent to X-radiation. With a suitable X-ray energy, transmission takes place essentially only in the grating gaps. The X-radiation passing through could be used to expose a photoresist applied on the rear side.

Semiconductor wafers (Si, Ge, GaAs, InP, . . . ) are also transparent to infrared radiation. This infrared radiation could also be employed for exposing the structures on the rear side when using a suitable IR-sensitive photoresist. Thin metallic layers and wafers transparent to ultraviolet light on the far side of a plasma frequency. This could similarly be employed for the lithography on the rear side. Many metals as well as other materials (Al, Si, . . . ) are transparent to neutrons. Neutron-sensitive resists may therefore likewise be used for lithography on the rear side.

As an alternative or in addition, however, it is also possible for at least two sub-gratings to be formed by different wafers.

It is also proposed that a filler material with a higher, preferably substantially higher, linear attenuation coefficient than the wafer material in the relevant energy range should be arranged in the grating gaps of at least one, precisely one or all the sub-gratings, in which case the filler material may comprise only a part of the height of the grating bars or flush-fill the grating gaps.

The Inventors also propose, in at least one embodiment, to align the sub-gratings mutually parallel in respect of their grating bars and grating gaps and are so that each ray passes either only through grating bars or only through grating gaps when crossing the sub-gratings.

If the transmission grating is used in a beam geometry which is designed to be fan-shaped or conical, then the sub-gratings arranged successively in the beam direction may comprise different grating periods, in which case the period increases from at least one sub-grating to a subsequent sub-grating, and the sub-gratings are arranged mutually aligned, so that the rays of the ray beam pass either only through grating gaps or only through grating bars.

In the transmission gratings according to at least one embodiment of the invention, the sub-gratings may furthermore be designed so that they are flat or curved in at least one plane around the radiation origin of the X-radiation passing through. As an alternative or supplementarily, the sub-gratings may include grating bars and grating gaps which are aligned in the beam direction.

If the transmission gratings according to at least one embodiment of the invention are being used not as absorption gratings but as phase gratings, then it may be advantageous that, for the sum of the sub-gratings, the height of the filler material in the gaps is dimensioned so that the X-radiation with the energy used for measuring the phase shift generates a phase shift of $\lambda/2$, and after the entire grating, at least in relation to the energy used for measuring the phase shift, the attenuation of the X-radiation is the same after passing through the bars and when passing through the filler material.

When phase gratings in grating-based phase contrast radiography are replaced by a plurality of sub-gratings, then it may be advantageous that, for the sum of the sub-gratings, the height of the filler material in the gaps is dimensioned so that between passage through the grating gaps/filler material and passage through the grating bars, (i) the X-radiation experiences a phase shift of $\pi$ or $\lambda/2$ and (ii) the intensity or transmission is the same for the photon energy caused to interfere in the interference pattern.

When analyzer gratings in grating-based phase contrast radiography are replaced by a plurality of sub-gratings, then it may be advantageous that, for the sum of the sub-gratings, the height of the filler material in the gaps is dimensioned so that between passage through the grating gaps/filler material and passage through the grating bars, the intensity or transmission is the same for the photon energy caused to interfere in the interference pattern.

As an alternative, the sub-gratings could also be designed so that, for each of the sub-gratings individually, the height of the filler material in the gaps is dimensioned so that the X-radiation with the energy used for measuring the phase shift generates a phase shift in the X-radiation of $\lambda/2$ and after each sub-grating, at least in relation to the energy used for measuring the phase shift, the attenuation of the X-radiation is the same when passing through the bars and when passing through the filler material.

The effect achieved in both variants of a phase grating as mentioned above is that, owing to the equal intensity of the rays which pass through the bars and the rays phase-shifted by $\pi$ relative thereto, which pass through the gaps and the filler material partially contained there, an optimally image formed interference pattern is generated with maximal intensity modulation and the least possible offset.

The image quality of phase contrast images and amplitude contrast depends on how accurately the phase and amplitude can be determined in each pixel. The ratio of the modulation to the offset is crucial in this regard (modulation transfer function of all components of the ray path). The intensity of the direct, undiffracted zeroth order ray also contributes to the offset and therefore to a quality reduction of the image. The aim must therefore be to reduce this component.

With respect to the arrangement of the sub-gratings of a transmission grating, according to the invention at least two of the sub-gratings may be aligned in the same direction or counter to one another with respect to the alignment of their grating bars; for sub-gratings without flush filler material in the grating gaps, it may be particularly favorable to place them only with their flat sides against one another so that no damage of the grating bars is possible by engaging in one another.

In respect of simpler alignment of the sub-gratings of a transmission grating, the Inventors propose, in at least one embodiment, that at least two sub-gratings arranged on separate wafers should be provided with markings, by which mutual alignment is facilitated.

At least one embodiment of the invention also relates to a focus-detector arrangement of an X-ray apparatus for generating projective or tomographic phase contrast recordings of a subject, which includes at least one of the X-ray optical gratings described above as a transmission grating.

At least one embodiment of the invention also relates to an X-ray system for generating projective phase contrast recordings, an X-ray C-arc system for generating projective or tomographic phase contrast recordings and an X-ray computer tomography system for generating tomographic phase contrast recordings, respectively equipped with an X-ray optical grating according to at least one embodiment of the invention.

BRIEF DESCRIPTION OF THE DRAWINGS

The invention will be explained in more detail below with the aid of example embodiments, only the features necessary for understanding the invention being represented. Here, the following references are used: 1: computer tomography system; 2: first X-ray tube; 3: first detector; 4: second X-ray tube; 5: second detector; 6: gantry housing; 7: patient; 8: patient support; 9: system axis; 10: control and computation unit; 11: memory; $D_1$: detector; d: distance; $E_x$: detector elements; $F_1$: focus; $G_0$: source grating; $G_1$: phase grating; $G_2$: analyzer grating; $G_{xy}$: sub-gratings; $g_0$, $g_1$, $g_2$: period of the grating lines; $h_0$, $h_1$, $h_2$: height of the grating bars; L: gaps; 1: distance; P: sample; $Prg_n$: program; S: bars; $S_i$: X-ray; x, y, z: Cartesian coordinates.

In detail, the figures show.

DETAILED DESCRIPTION OF THE EXAMPLE EMBODIMENTS

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or", includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the", are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

For better understanding, the structure of a focus-detector arrangement with X-ray optical gratings according to an embodiment of the invention, which allow phase contrast measurement, will be presented at first. In this regard it should essentially be noted that the figures are not shown true to scale, rather they are intended to highlight the basic structure and the described effects. The transverse axis is expanded relative to the longitudinal axis (=optical axis). The angles are therefore represented with an exaggerated size. For didactic reasons, the interference pattern and the analyzer grating in particular have been shown somewhat spatially separated from one another, even though it is precisely the object of the method to position the analyzer grating at the maximum of the interference pattern, i.e. at the Talbot distance. The dimensions d and $r_2$ therefore refer both to the interference pattern and to the analyzer grating.

Figure 1:
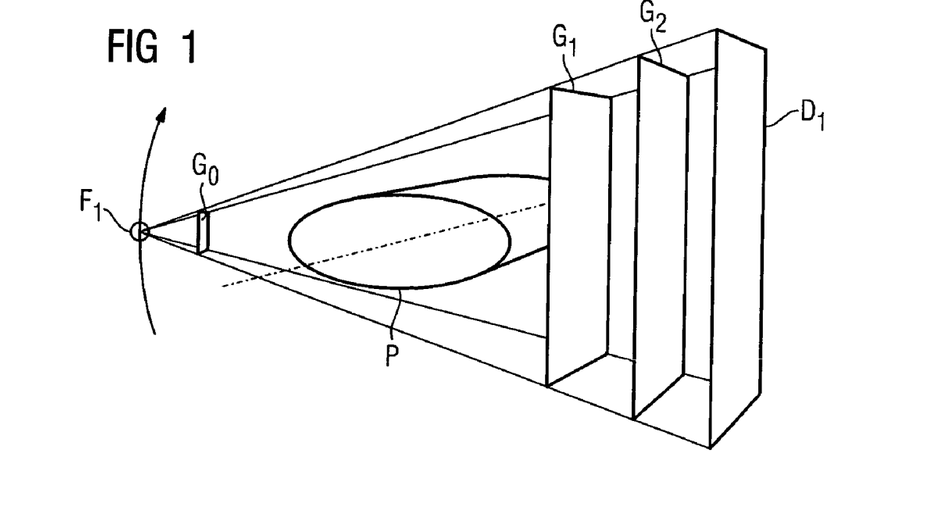
FIG. 1: schematic 3D representation of a focus-detector system with a grating set for determining phase shifts.

FIG. 1 shows a schematic 3D representation of a focus-detector system of an X-ray computer tomography system with a sample P lying in the beam path as a subject. The focus $F_1$ on the detector $D_1$ are arranged on a gantry (not represented here) and move circularly around the system axis shown by dots and dashes. If a linear movement of the patient or sample P in the system axis direction is additionally carried out during the rotation of the focus-detector system, then this leads to spirally shaped scanning of the patient or sample P which is known per se. Three X-ray optical gratings $G_0$, $G_1$ and $G_2$ are arranged in the beam path of the focus-detector system, the first grating $G_0$, which is also referred to as a source grating, being applied in the immediate vicinity of the focus $F_1$ and having the X-radiation pass through it.

In the propagation direction of the X-radiation, this is followed by the actual subject P. Before the detector $D_1$ lying on the other side of the system axis, there first follows the second grating $G_1$ referred to as a phase grating. This is followed in the radiation direction by the third grating $G_2$, referred to as an analyzer grating, which is advantageously arranged immediately in front of the detector $D_1$. The detector $D_1$ is a position resolving detector. During the scan, the connecting lines between the focus $F_1$ and the individual detector elements respectively represent an X-ray arranged in space, the intensity variation of which is measured by the respective detector element.

The grating lines should preferably be oriented perpendicularly to the optical axis, i.e. perpendicularly to the midline between the focus and detector midpoints, and the grating lines of the individual gratings should extend mutually parallel. This applies strictly for plane gratings and at least approximately also for curved gratings.

Certain geometrical conditions should be complied with for phase contrast measurement. These are represented in more detail in FIG. 2. This figure shows a focus-detector system according to the invention with a grating set $G_0$ to $G_2$. The focus $F_1$ lies before the first grating $G_0$. The first grating $G_0$ has a grating line period $g_0$ and a grating bar height $h_0$. The gratings $G_1$ and $G_2$ are correspondingly also provided with a height $h_1$ and $h_2$, respectively, and a period $g_1$ and $g_2$, respectively. For the function of the method according to an embodiment of the invention, it is necessary for the distance 1 between the gratings $G_0$ and $G_1$ and the distance d between the gratings $G_1$ and $G_2$ to be in a particular mutual ratio. This ratio has been described above in Equation (2).

Figure 2:
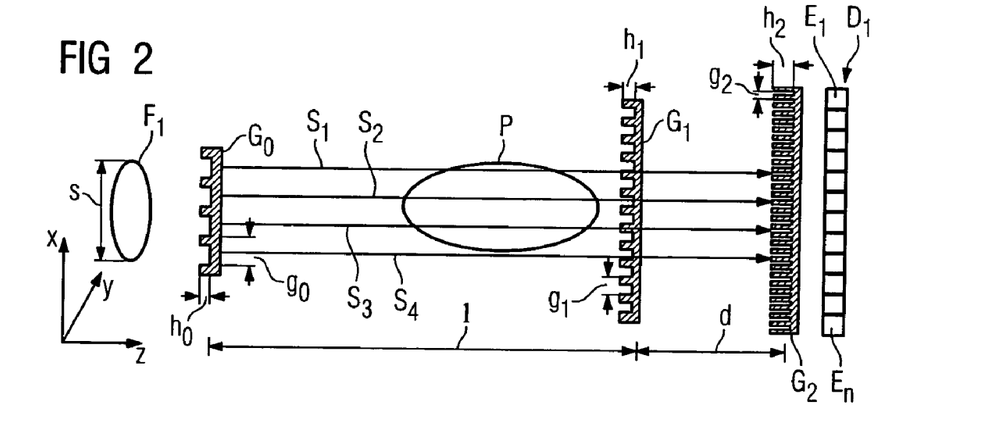
FIG. 2: longitudinal section through a focus-detector system with representation of a source grating, a phase grating and an analyzer grating and their grating structure.

The distance of the detector $D_1$ with its detector elements $E_1$ to $E_n$ from the last grating $G_2$ is not essential. The height $h_1$ of the bars of the phase grating should be selected so that a phase shift by one half wavelength compared to the gaps is obtained according to the relevant energy of the X-radiation.

It is also essential is that the height $h_2$ of the analyzer grating is sufficient in order to generate effective absorption differences between the bars through which the X-radiation passes and the substantially free positions of the grating, in order to obtain a corresponding interference pattern/standing wave field on the rear side.

It should be pointed out that in this embodiment of a focus-detector arrangement, a point-like focus may be replaced by an extended focus if the extended focus is combined with a source grating as described in the introduction, so that the necessary coherence condition for the described phase contrast measurement is fulfilled.

Figure 3:
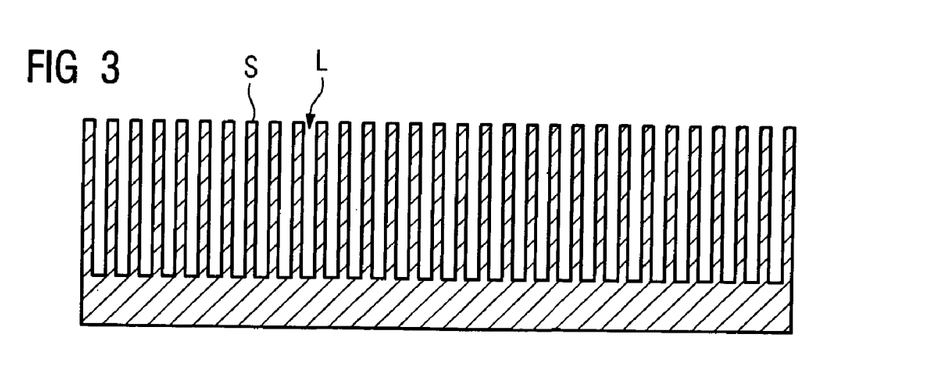
FIG. 3: a single X-ray optical grating.

In the X-ray optical gratings as presented above, the problem usually arises that they must have grating bars whose height is large relative to the spacing of the bars. The known embodiment of such an example grating is shown in FIG. 3. This grating comprises bars S and gaps L between them, which are impressed into the surface of a wafer, for example by etching processes.

Figure 4:
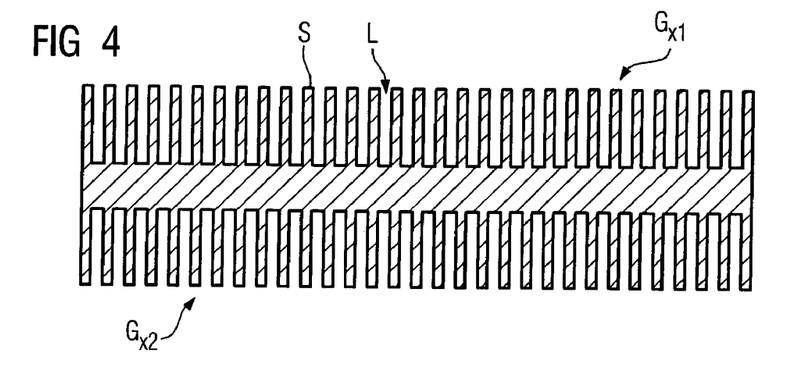
FIG. 4: an X-ray optical grating as a double sub-grating on a common wafer.

According to an embodiment of the invention, this production problem is circumvented by using a combination of a plurality of sub-gratings arranged in direct succession, instead of a single grating with a particular function, these being assembled so that they correspond in their overall effect to the single first grating. A first example of this is represented in FIG. 4. Here, two sub-gratings are generated on the two sides of a common wafer, each individual structure being substantially simpler to produce owing to the now lower depth of the grating gaps. Moreover, the problem of accurate mutual alignment is also resolved here since a common wafer is used.

Figure 5:
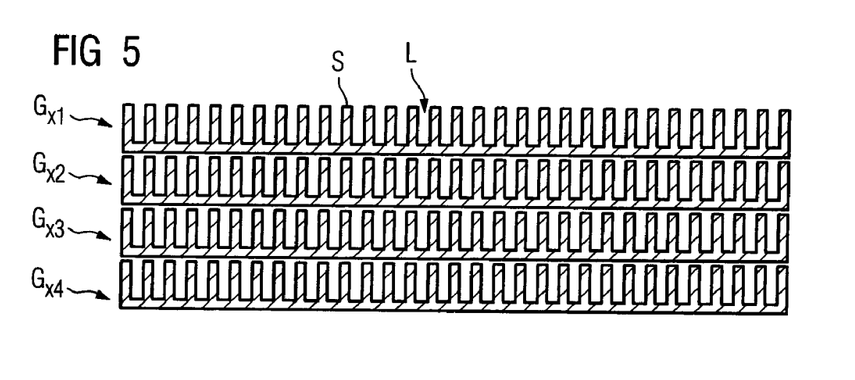
FIG. 5: an X-ray optical grating including four identical sub-gratings.

Another variant of an embodiment of an X-ray optical grating according to the invention, by combining a plurality of sub-gratings—here four sub-gratings—is shown in FIG. 5.

Here, there are four identical and equally aligned sub-gratings $G_{x1}$ to $G_{x4}$—the index "x" stands for the index of one of the gratings $G_0$ to $G_2$ of the focus-detector arrangement in FIGS. 1 and 2—with only ¼ of the grating bar height of the grating $G_x$ otherwise to be replaced.

With respect to simpler alignment of the sub-gratings, the Inventors propose, in an embodiment, that at least two sub-gratings arranged on separate wafers should be provided with markings, by which mutual alignment is facilitated Fine adjustment of the phase grating and the analyzer grating could also be carried out piecewise. A first phase grating and a first analyzer grating are used. Since the phase grating is too thin for an optimal layout, the resulting standing wave field is only poorly pronounced, but nevertheless present. The grating can thus be aligned with the aid of the standing wave field:
1. Alignment of the grating position along the optical axis of the layout: The periods of the phase grating and of the analyzer grating are interlinked, in the case of a cone beam geometry by:

$$g_2 = \frac{1}{2} \frac{r_1 + d}{r_1} g_1$$

where d is the distance between the gratings, $r_1$ is the distance between the source and the first grating, $g_2$ is the period of the analyzer grating $G_2$, which is equal to the transverse period of the standing wave field, $g_1$ is the period of the phase grating $G_1$.

If this condition is not fulfilled then an interference pattern is not obtained on a detector placed behind the analyzer grating, but instead a so-called division moiré pattern, consisting of shadow lines which are parallel to the grating bars. This is the case, for example, whenever the phase grating is displaced along the optical axis relative to the intended position. The gratings may then be aligned in the position along the beam axis by displacing them so that this pattern vanishes.
2. Parallel Alignment of the Grating Lines:

If the grating lines of the analyzer grating are not parallel to the standing wave field (and therefore to the grating lines of the phase grating) then an interference pattern is not obtained on a detector placed behind the analyzer grating, but instead a so-called rotation moiré pattern consisting of shadow lines which are perpendicular to the grating bars. The grating lines may then be aligned parallel by rotating the phase grating so that this pattern vanishes.

In practice, a superposition of a rotation and a division moiré pattern can take place. This does not change anything for the principle of aligning the gratings in respect of angle and distance. The grating lines may firstly be aligned parallel by rotating the grating so that a pure division moiré is observed on the detector, i.e. a moiré pattern with shadow lines which are parallel to the grating lines. The spacing of the gratings is then corrected as described above. As an alternative, the grating position may firstly be aligned along the optical axis by displacing the grating until a pure rotation moiré is observed on the detector, i.e. a moiré pattern with shadow lines which are perpendicular to the grating lines. The rotation of the gratings is then corrected as described above.

If a further incorrectly aligned grating is added to the correctly aligned gratings, the standing wave field is perturbed. A moiré pattern is then created in the same way as described above. The added phase grating will be aligned in the same way as the first grating. Further gratings are added in the same way.

It should be pointed out that it lies within the scope of the embodiments of the invention to configure the orientation of the individual sub-gratings arbitrarily, so long as the grating gaps and the grating bars are respectively arranged successively as seen in the beam direction. This applies for all variants of sub-grating combinations in this document.

Figure 6:
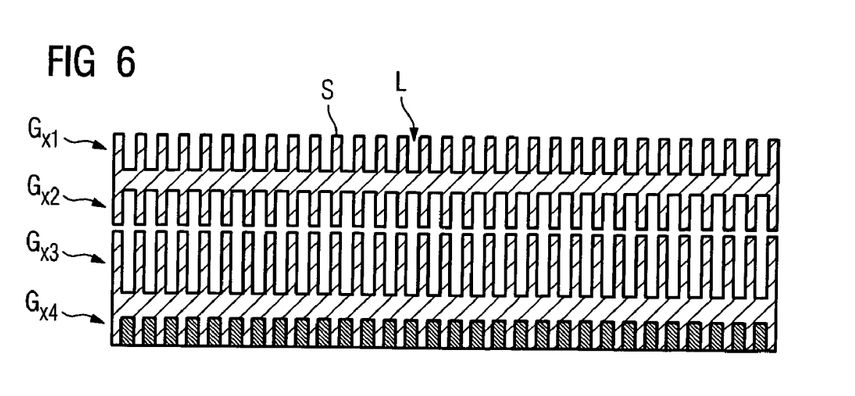
FIG. 6: an X-ray optical grating including two double sub-gratings with filler in one sub-grating.

FIG. 6 shows another variant of a sub-grating combination according to the invention with two different double gratings $G_{x1}$, $G_{x2}$ and $G_{x3}$, $G_{x4}$, the lower of the double gratings $G_{x3}$, $G_{x4}$ additionally comprising a filler material in the gaps L of one grating, which ensures uniform absorption of the X-radiation over the entire grating, the rays which pass through neighboring gaps L and bars S experiencing a phase shift by π. Additionally, but not compulsorily, the lower double grating here is designed in respect of its bar heights so that the filler terminates flush with the grating bars.

Figure 7:
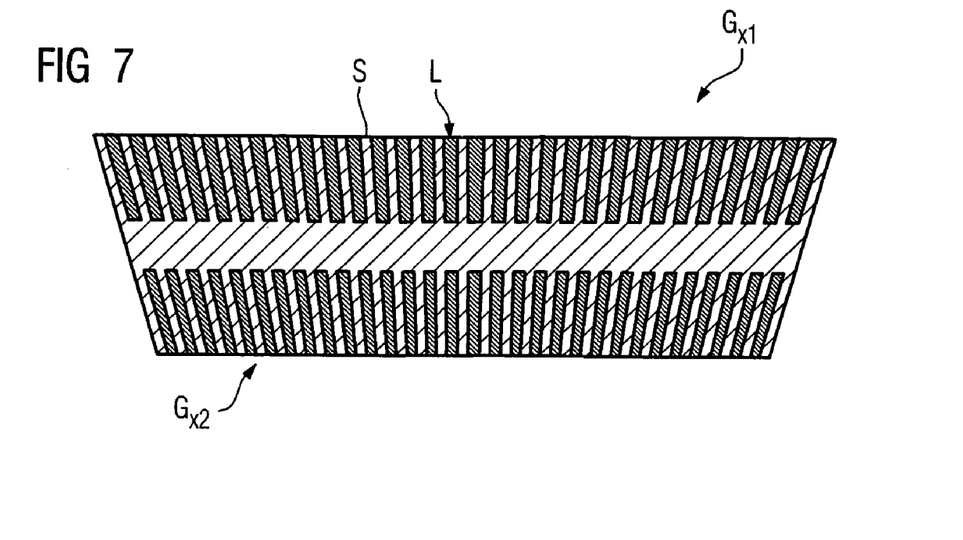
FIG. 7: an X-ray optical grating as a double sub-grating on a common wafer, with flush-filling of the grating gaps on both sides and radially aligned grating bars.
Figure 8:
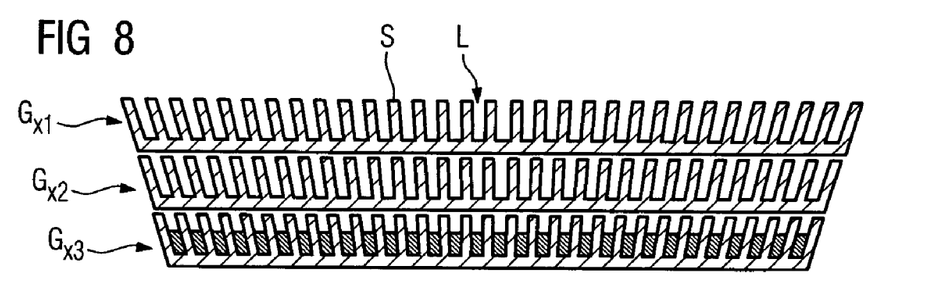
FIG. 8: an X-ray optical grating including three identical sub-gratings with radially aligned grating bars and partial filling in the lower sub-grating.
Figure 9:
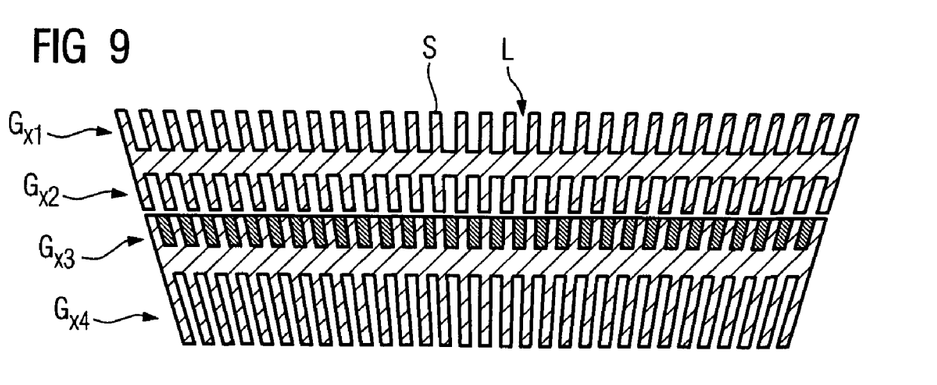
FIG. 9: an X-ray optical grating including two double sub-gratings with filler in one sub-grating, with radially aligned grating bars.

FIGS. 7 to 9 show alternative embodiments of FIGS. 5 to 6 with a flat sub-gratings, although in this case the alignment of the grating bars and grating gaps is adapted according to the radial alignment of the radiation. The grating of FIG. 7 is furthermore completely filled with filler material in the gaps so that it acts as an absorption grating, i.e. a source grating or analyzer grating. The gratings of FIGS. 8 and 9 are configured as phase gratings with uniform absorption over the entire grating surface, as described with reference to FIG. 6.

Figure 10:
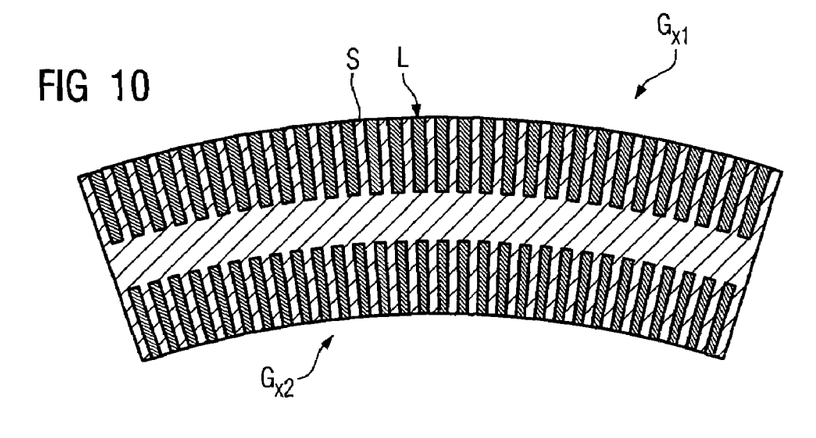
FIG. 10: an X-ray optical grating including as a double sub-grating on a common wafer, with flush-filling of the grating gaps on both sides and a design curved around the focus.
Figure 11:
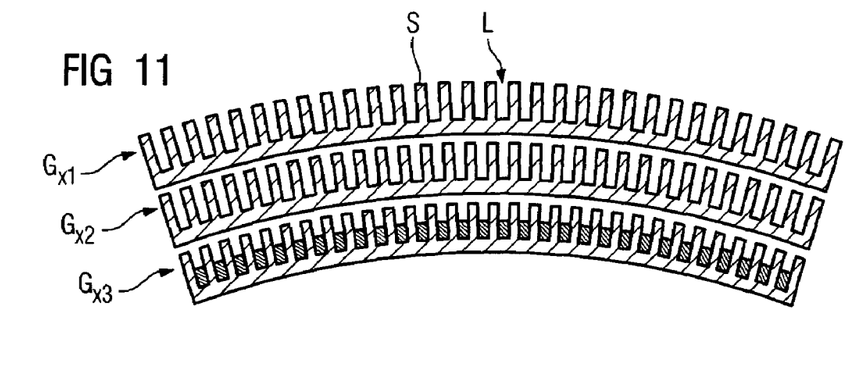
FIG. 11: an X-ray optical grating, including three identical sub-grating this with a design curved around the focus and partial filling in the lower sub-grating.
Figure 12:
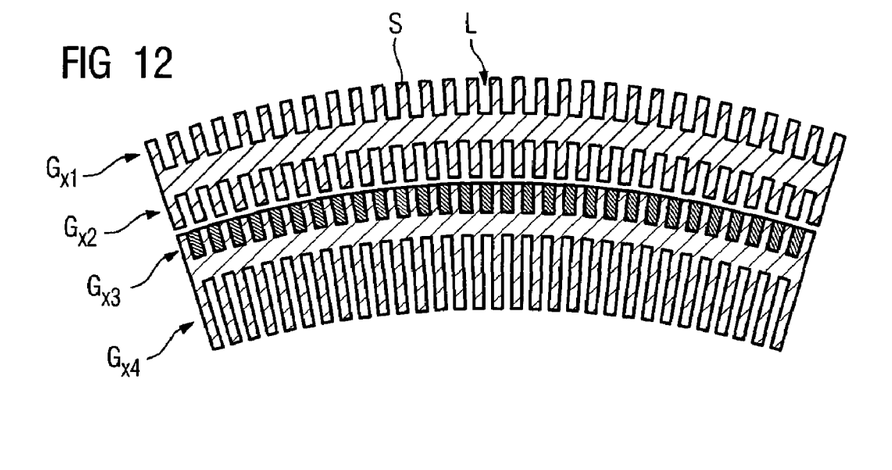
FIG. 12: an X-ray optical grating including two double sub-gratings with filler in one sub-grating, with radially aligned grating bars and a design curved around the focus.

Lastly, FIGS. 10 to 12 show embodiments corresponding to FIGS. 7 to 9, but in this case the sub-gratings are configured with a curvature around the radiation centre, i.e. the focus. Here again, the grating bars S are respectively aligned radially with the focus so that no shadowing of the individual rays occurs in the edge regions of the grating gaps when passing through the sub-gratings.

In addition, platelets or films of small height, which prevent possible mutual damage of the grating structures, may be placed between all the sub-gratings presented here without departing from the scope of the invention.

Figure 13:
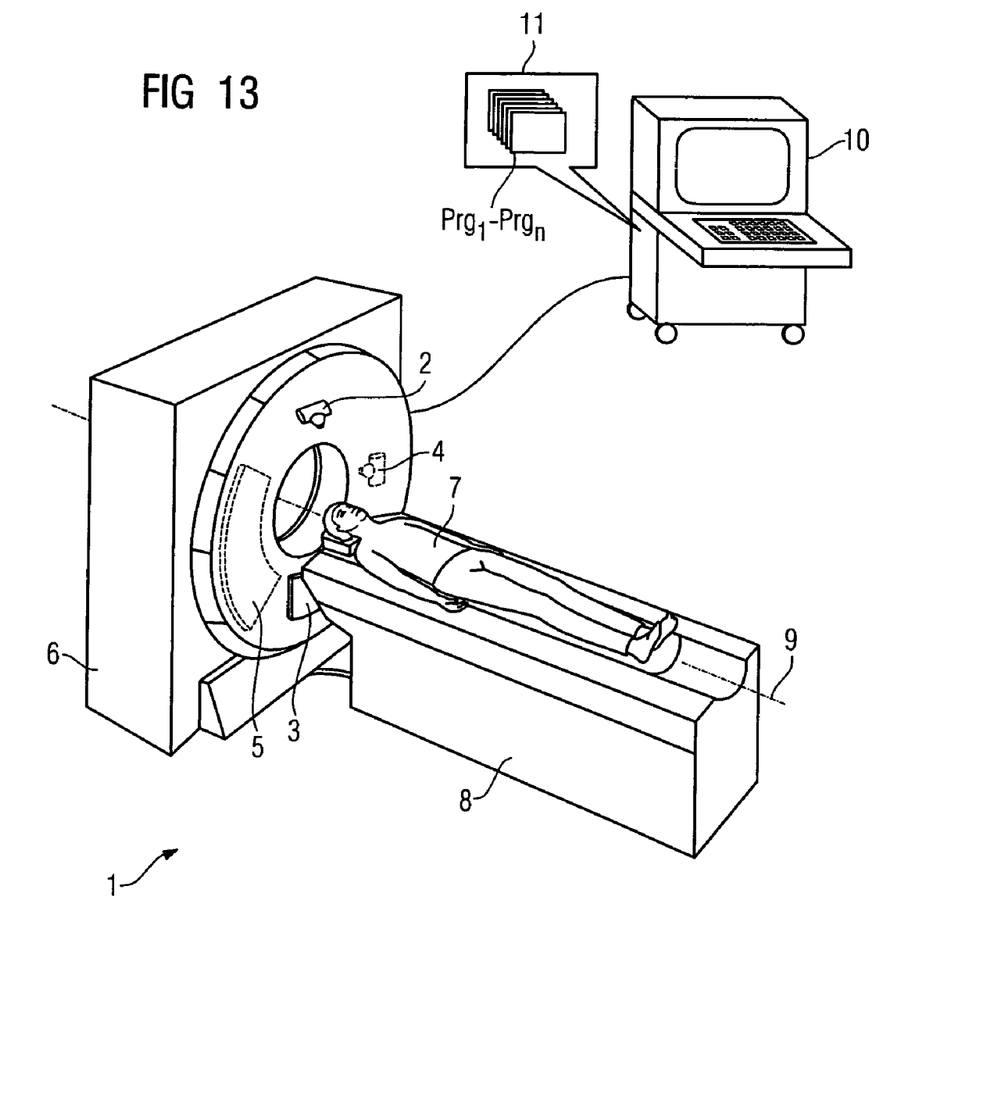
FIG. 13: an X-ray computer tomography system in 3D view with a focus-detector system according to an embodiment of the invention.

FIG. 13 represents a complete computer tomography system with focus-detector systems according to an embodiment of the invention for carrying out the method according to an embodiment of the invention, by way of example and also generically for other X-ray systems, in particular X-ray systems for generating projective phase contrast recordings and for C-arc equipment. This figure shows the computer tomography system 1 which comprises a first focus-detector system with an X-ray tube 2 and a detector 3 lying opposite, which are arranged on a gantry (not represented in detail) in a gantry housing 6. An X-ray optical grating system according to an embodiment of the invention with gratings composed of sub-gratings is arranged in the beam path of the first focus-detector system 2, 3 so that the patient 7, who lies on a patient support 8 displaceable along the system axis 9, can be displaced into the beam path of the first focus-detector system and scanned there. The computer tomography system is controlled by a computation and control unit 10 in which programs $Prg_1$ to $Prg_n$ are stored in a memory 11, which carry out the method according to an embodiment of the invention as described above and reconstruct corresponding tomographic images from the measured ray-dependent phase shifts.

Instead of a single focus-detector system, a second focus-detector system may optionally be arranged in the gantry housing. This is indicated in the representation by the X-ray tube 4 shown in dashes and the detector 5 represented in dashes.

At least in one focus-detector system, there is a grating according to an embodiment of the invention in which the grating structure, which is required for the detection of phase contrast recordings, is generated in the grating medium by an ultrasound standing wave.

Moreover, it should also be pointed out that the focus-detector systems as presented are not only capable of measuring phase shifts of the X-radiation, rather they are furthermore suitable for conventional measurement of the radiation absorption and the reconstruction of corresponding absorption recordings. Optionally, combined absorption and phase contrast recordings may even be generated.

It is furthermore to be pointed out that the medical computer tomography systems presented in this patent application are merely intended to be an example representation of an alternative application of the invention. Embodiments of the invention may likewise be used in conjunction with systems for examining biological or inorganic samples, without departing from the scope of this application. In particular, embodiments of the invention are applicable to systems for material analysis.

It is to be understood that the features of the invention as mentioned above may be used not only in the combination respectively indicated, but also in other combinations or in isolation, without departing from the scope of the present invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray optical transmission grating of a focus-detector arrangement of an X-ray apparatus for generating at least one of projective and tomographic phase contrast recordings of a subject, comprising:
   at least one wafer including a multiplicity of grating bars and grating gaps, the grating bars and grating gaps being arranged periodically on at least one surface of the at least one wafer, wherein the X-ray optical transmission grating includes at least two sub-gratings arranged in direct succession in a beam direction, wherein a beam profile of a transmitted X-radiation is designed to be at least one of fan-shaped and conical, and the sub-gratings arranged successively in the beam direction comprise different grating periods, and wherein a grating period increases from at least one sub-grating to at least one subsequent sub-grating and the sub-gratings are arranged to be mutually aligned, so that the rays of the beam pass through only one of either of the grating gaps or the grating bars.

2. An X-ray optical transmission grating of a focus-detector arrangement of an X-ray apparatus for generating at least one of protective and tomographic phase contrast recordings of a subject, comprising:
   at least one wafer including a multiplicity of grating bars and grating gaps, the grating bars and grating gaps being arranged periodically on at least one surface of the at least one wafer, wherein the X-ray optical transmission grating includes at least two sub-gratings arranged in direct succession in a beam direction, wherein a filler material with a relatively higher linear attenuation coefficient than the wafer material in the relevant energy range is arranged in the grating gaps of at least one sub-grating, wherein the transmission grating is a phase grating and, for the sum of the sub-gratings, the height of the filler material in the gaps is dimensioned so that the X-radiation with the energy used for measuring the phase shift generates a phase shift of $\lambda/2$ in the X-radiation and after the entire grating, at least in relation to the energy used for measuring the phase shift, the attenuation of the X-radiation is the same after passing through the bars and when passing through the filler material.

3. An X-ray optical transmission grating of a focus-detector arrangement of an X-ray apparatus for generating at least one of projective and tomographic phase contrast recordings of a subject, comprising:
   at least one wafer including a multiplicity of grating bars and grating gaps, the grating bars and grating gaps being arranged periodically on at least one surface of the at least one wafer, wherein the X-ray optical transmission grating includes at least two sub-gratings arranged in direct succession in the beam direction, wherein a filler material with a relatively higher linear attenuation coefficient than the wafer material in the relevant energy range is arranged in the grating gaps of at least one sub-grating, wherein the transmission grating is a phase grating and, for each of the sub-gratings individually, the height of the filler material in the gaps is dimensioned so that the X-radiation with the energy used for measuring the phase shift generates a phase shift in the X-radiation of $\lambda/2$ and after each sub-grating, at least in relation to the energy used for measuring the phase shift, the attenuation of the X-radiation is the same when passing through the bars and after passing through the filler material.

4. The transmission grating as claimed in claim 1, wherein at least two sub-gratings arranged on a separate wafers comprise markings by which mutual alignment is made possible.

5. A focus-detector arrangement of an X-ray apparatus for generating at least one of projective and tomographic phase contrast recordings of a subject, wherein at least one of X-ray optical gratings used is designed as the transmission grating of claim 1.

6. The transmission grating as claimed in claim 2, wherein at least two sub-gratings arranged on a separate wafers comprise markings by which mutual alignment is made possible.

7. The transmission grating as claimed in claim 3, wherein at least two sub-gratings arranged on a separate wafers comprise markings by which mutual alignment is made possible.

8. A focus-detector arrangement of an X-ray apparatus for generating at least one of projective and tomographic phase contrast recordings of a subject, wherein at least one of X-ray optical gratings used is designed as the transmission grating of claim 2.

9. A focus-detector arrangement of an X-ray apparatus for generating at least one of projective and tomographic phase contrast recordings of a subject, wherein at least one of X-ray optical gratings used is designed as the transmission grating of claim 3.

10. An X-ray system for generating projective phase contrast recordings, comprising the X-ray optical transmission grating of the focus-detector arrangement of claim 1.

11. An X-ray system for generating projective phase contrast recordings, comprising the X-ray optical transmission grating of the focus-detector arrangement of claim 2.

12. An X-ray system for generating projective phase contrast recordings, comprising the X-ray optical transmission grating of the focus-detector arrangement of claim 3.

13. An X-ray C-arc system for generating projective or tomographic phase contrast recordings, comprising the X-ray optical transmission grating of the focus-detector arrangement of claim 1.

14. An X-ray C-arc system for generating projective or tomographic phase contrast recordings, comprising the X-ray optical transmission grating of the focus-detector arrangement of claim 2.

15. An X-ray C-arc system for generating projective or tomographic phase contrast recordings, comprising the X-ray optical transmission grating of the focus-detector arrangement of claim 3.

16. An X-ray computer tomography system for generating tomographic phase contrast recordings, comprising the X-ray optical transmission grating of the focus-detector arrangement of claim 1.

17. An X-ray computer tomography system for generating tomographic phase contrast recordings, comprising the X-ray optical transmission grating of the focus-detector arrangement of claim 2.

18. An X-ray computer tomography system for generating tomographic phase contrast recordings, comprising the X-ray optical transmission grating of the focus-detector arrangement of claim 3.

* * * * *